United States Patent [19]
Glynn

[11] Patent Number: 5,432,882
[45] Date of Patent: Jul. 11, 1995

[54] AUTOMATIC ELECTRICALLY HEATED CIGARETTE LIGHTER SOCKET INSERTED MOTOR VEHICLE DEODORIZER DEVICE

[75] Inventor: Johanne M. Glynn, Flemington, N.J.

[73] Assignee: Ideal Ideas, Inc., Flemington, N.J.

[21] Appl. No.: 119,536

[22] Filed: Sep. 13, 1993

[51] Int. Cl.⁶ .............................................. A61L 9/03
[52] U.S. Cl. .................................. 392/392; 392/390;
392/391; 392/395
[58] Field of Search ............... 392/386, 390, 391, 395;
422/124, 125; 261/142, DIG. 65

[56] References Cited

U.S. PATENT DOCUMENTS

| | | | |
|---|---|---|---|
| 2,612,432 | 9/1952 | Boddy | 422/125 |
| 2,881,303 | 4/1959 | Resk | 392/390 X |
| 4,574,181 | 3/1986 | Spector . | |
| 4,604,245 | 8/1986 | Gutierrez . | |
| 4,686,353 | 8/1987 | Spector . | |
| 4,687,904 | 8/1987 | Melanson et al. | 392/390 |
| 4,692,590 | 9/1987 | Spector . | |
| 4,707,338 | 11/1987 | Spector | 422/124 |
| 4,780,286 | 10/1988 | Parent et al. | 422/125 |
| 4,808,347 | 2/1989 | Dawn | 422/124 |
| 5,111,477 | 5/1992 | Muderlak | 392/390 |

FOREIGN PATENT DOCUMENTS

| | | | |
|---|---|---|---|
| 2626452 | 8/1989 | France | 392/386 |
| 55-23853 | 2/1980 | Japan | 392/395 |
| 2062199 | 5/1981 | United Kingdom | 392/390 |
| 2211415 | 9/1981 | United Kingdom | 392/390 |

*Primary Examiner*—Teresa J. Walberg
*Attorney, Agent, or Firm*—Kenneth P. Glynn

[57] ABSTRACT

An automatic motor vehicle deodorizer device, adapted for insertion into a motor vehicle cigarette lighter socket having two terminals to provide electrical energy. The device is adapted to receive a vaporizable deodorizing agent. The device contains a power controller which automatically controls power to an internal heating element. The heating element is activated so long as the vaporizable deodorizing agent is above a precalibrated minimum size. The device contains an optional timer for activating the power controller. An optional override switch allows manual control of the heating element.

16 Claims, 3 Drawing Sheets

AUTOMATIC ELECTRICALLY HEATED CIGARETTE LIGHTER SOCKET INSERTED MOTOR VEHICLE DEODORIZER DEVICE

BACKGROUND OF THE INVENTION

1. Field of the Invention

The present invention relates to an automatic motor vehicle deodorizer device which is insertable (at least partially) into a motor vehicle cigarette lighter socket. It is specifically directed to such devices that are inserted into the sockets of motor vehicle cigarette lighters and make immediate and continuous connection with the terminals of the sockets. Electrical power controllers of the devices selectively activate the electrical heater units to evaporate deodorant agent without the need for pushing the device further into the socket for each use.

2. Information Disclosure Statement

The present invention deodorizer device is based on the needs of drivers and passengers to remove stale or bad odors from the cabin of a motor vehicle, as well as to add pleasant odors thereto. Thus, the term "deodorizer agent" should be construed broadly to mean vaporizable materials which take away odors, those which shield odors and those which add pleasant odors.

Aroma-generating automobile cigarette lighter devices are known. U.S. Pat. Nos. 4,574,181, 4,686,353 and 4,692,590, all three issued to Donald Spector, describe cigarette lighter type devices that operate with the use of bimetallic materials for release of the device and removal of contacts from the lighter socket terminals upon each use. These devices evaporate a deodorizer or aromatic material utilizing power from the cigarette lighter, but must be pushed in for each use. Further, these prior art rely upon direct resistance heater systems with or without thermal conductance and have no power controllers.

U.S. Pat. No. 4,604,245 is directed to a perfume dispensing device which requires separate mounting and wiring within the dashboard, as well as a separate motor and impeller blades.

The present invention does not require a motor, am impeller, or a separate wiring in the dashboard. Further, it does not utilize the direct-contact-with-the-socket type heaters, does not require pushing in for each use and may be set to deodorize automatically at predetermined intervals.

SUMMARY OF THE INVENTION

An automatic motor vehicle deodorizer device, adapted for insertion into a motor vehicle cigarette lighter socket. The socket having two terminals to provide electrical energy to the device. The device includes a generally cylindrical housing which can be at least partially inserted into the socket. The end of the housing is adapted to receive a vaporizable deodorizing agent. To vaporize the deodorizing agent, the device contains a heating unit. The heating unit is regulated by an electric power controller contained within the housing, the electric power controller automatically opens the circuit when the vaporizable deodorizing agent in the housing falling below a precalibrated minimum and automatically closes the circuit only so long as the vaporizable deodorizing agent in the housing exceeds a precalibrated minimum. The circuit electrically connects the heater unit to two terminal contacts, these contacts sufficiently contact the socket's terminals to conduct electricity and energize the circuit. When the electric power controller automatically opens and closes the circuit, the heater is turned on and off, and consequently the vaporization of the deodorizing agent is moderated. Thus, the device can remain in the cigarette lighter socket, in constant contact with the terminals.

BRIEF DESCRIPTION OF THE DRAWINGS

For a better understanding of the invention as well as other objects and further features thereof, reference is made to the following detail description to be read in conjunction with the accompanying drawings, wherein.

DETAILED DESCRIPTION OF THE PRESENT INVENTION

The present invention is directed to odor and air problems related to motor vehicles. It is also directed to a device which will discourage smoking by occupying the socket of a motor vehicle cigarette lighter, and will release evaporatable material ("deodorizer", as defined above) which will provide a aroma to drivers and passengers and/or eliminate, decrease or cover undesirable odors.

The present invention also provides a device which may continuously or intermittently automatically evaporate deodorizer agent at predetermined intervals.

Thus, the present invention may be disposable, but is preferably reusable. It may evaporate deodorizer agent for only a small time each day or hour or portion thereof, depending upon the particular embodiment, and/or it may function only upon insertion of a deodorizer agent cartridge and shut off when the cartridge has lost all or most of its mass.

Significantly, the present invention device need not be pushed further into a cigarette lighter socket to be activated. The terminals of the cigarette lighter socket are in direct and continuous conductive connection with terminal contacts of the present invention device, ready to energize a heater unit when a controller of the present invention device completes a circuit within the present invention device.

Figure 1:
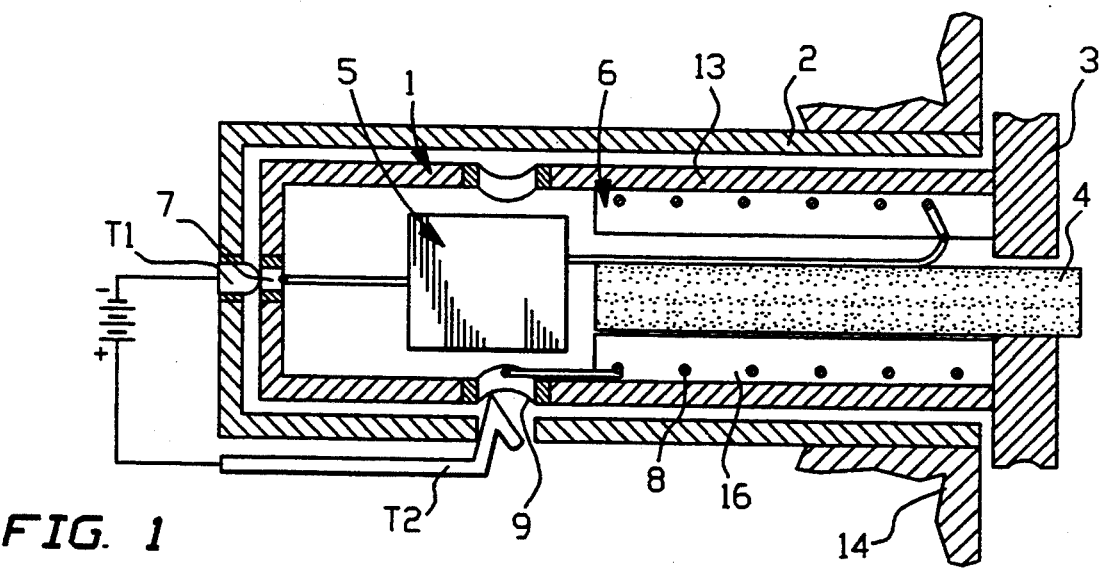
FIG. 1 shows the device with automatic electrical power controller.

Referring to FIG. 1, the automatic motor vehicle deodorizing device 1 includes a cylindrical housing 1 which is adapted to fit in a cigarette lighter socket 2 mounted in a dashboard of a motor vehicle 14. Housing 13 has an angular flange 3 on its front end having an opening adapted to receive a vaporizable deodorizing agent 4.

Heater unit 6 fits within housing 13, and has a bore running axially to receive deodorizing agent 4. Heater unit 6 contains a resistor wire 8 to provide heat, and an insulating material 16 having a high heat capacity to absorb, diffuse and retain heat. Heater unit 6 generates sufficient heat to vaporize the deodorizing agent 4. Heater unit 6 is regulated by electric power controller 5. The electrical circuit is comprised of contact 7 which is in electrical contact with terminal T1 of the vehicle cigarette lighter socket 2. One end of the power controller 5 is in electrical contact with contact 7. The other end of the power controller 5 is in electrical contact with one end of the resistor wire 8. The other end of the resistor wire 8 is in electrical contact with contact 9. Contact 9 is in electrical contact with terminal T2 of the vehicle cigarette lighter socket 2. When the device 1 is inserted into the vehicle cigarette lighter socket 2, terminals T1 and T2 provide a means for providing electrical power to the electrical circuit.

Figure 1A:
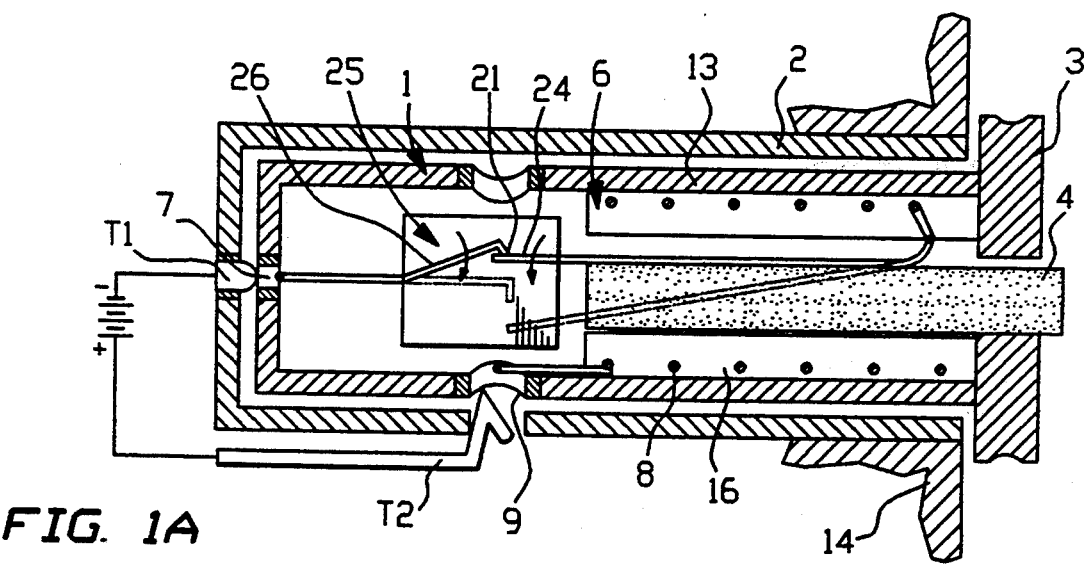
FIG. 1A shows a preferred embodiment of the automatic electric power controller.
Figure 1B:
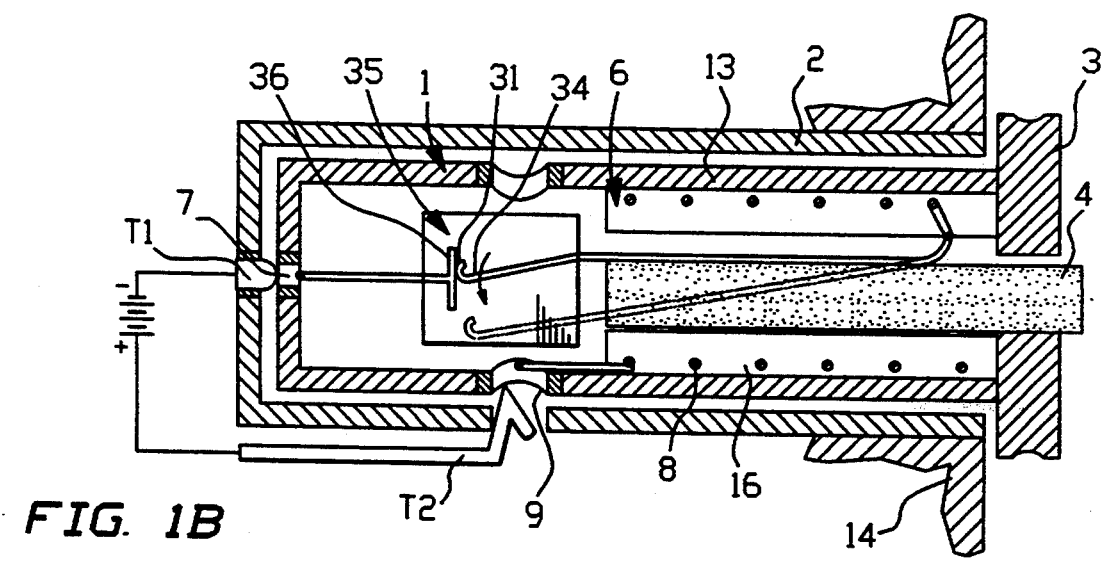
FIG. 1B shows another embodiment of the automatic electric power controller.
Figure 1C:
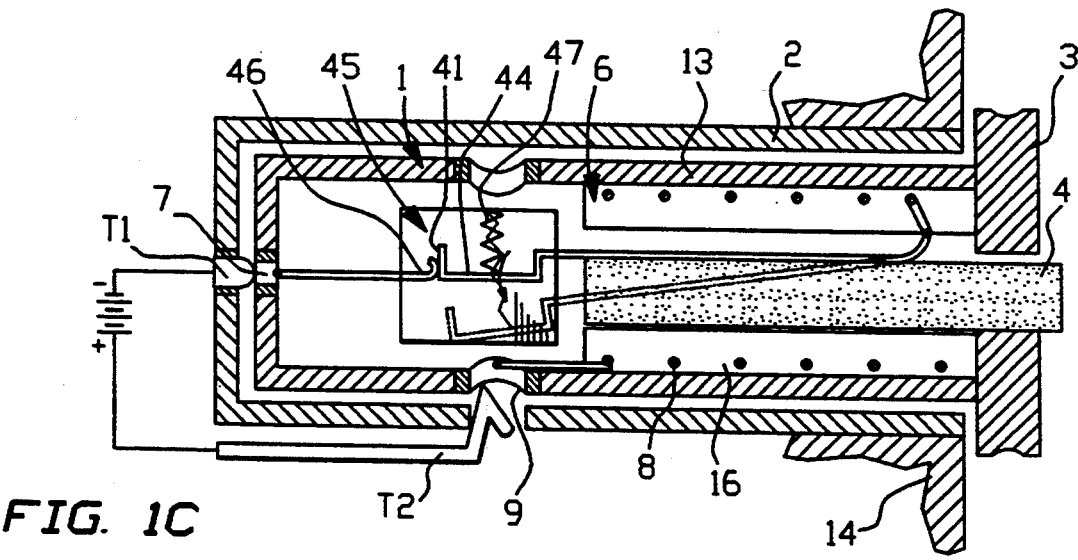
FIG. 1C shows another embodiment of the automatic electric power controller.

Electric power controller 5 has several preferred embodiments, each of which regulates the device so that it can remain in socket 2, in constant contact with terminals T1 and T2. In FIGS. 1A, 1B and 1C, power controller 25, 35 and 45 respectively is designed to open a sensing switch 11 in electrical circuit when the volume of deodorizing agent 4 reaches a predetermined minimum. The sensing switch 21, 31, and 41, respectively comprises a sensing conductor 9 and a supply conductor 26, 36 and 46 respectively. Sensing conductor 34 and 44 respectively has two ends, one end which is electrically connected to the resistor wire 8 and a movable end which is adapted so that it electrically contacts with the supply conductor 26, 36 and 46 respectively. Additionally, sensing conductor 24, 34 and 44 respectively comprises a forcing means to urge the sensing conductor 24, 34 and 44 respectively against deodorizing agent 4. As the agent vaporizes, and consequently diminishes in diameter, the movable end of the sensing conductor 24, 34 and 44 respectively moves. The movable end remains in contact with the supply conductor 26, 36 and 46 respectively while the volume of deodorizing agent 4 in housing 3 exceeds the precalibrated minimum. However, when deodorizing agent 4 diminishes to a precal, sensing conductor 24, 34 and 44 respectively will move such that movable end loses electrical contact with the supply conductor 26, 36 and 46 respectively. Consequently, the circuit will open, and heater unit 6 will de-energize.

In FIG. 1A, sensing conductor 24 has a bias urging it against deodorizing agent 4, and supply conductor 26 has a bias urging it against the movable end of the sensing conductor 24. This configuration offers at least two benefits. First, the urging of the supply conductor 26 against movable end of the sensing conductor 24 which adds to the urging of sensing conductor 24 against deodorizing agent 4. Second, it closes the electric circuit, and thereby energizes heater unit 6. The electric circuit remains closed and heater unit 6 energized until the diameter of the deodorizing agent 4 diminishes to a precalibrated minimum where floating end 17 moves such that it loses electrical contact with the supply conductor 26.

In FIG. 1B, although sensing conductor 34 still has a bias towards the center of the housing 13, the supply conductor 36 exhibits no bias. Variable position contactor 10, having an angular electrical 19, maintains contact with floating end 17 as floating end 17 moves in association with the vaporization of deodorizing agent 4. When deodorizing agent 4 reaches a precalibrated minimum, the movable end of the sensing conductor 34 loses electrical contact with the supply conductor 36. In FIG. 1C, the sensing conductor 44 uses a spring 12 to urge it against deodorizing agent 4. Like the embodiment of FIG. 1B, the supply conductor 46 remains fixed. The supply conductor 46 is adapted to be in electrical contact with the sensing conductor 44 only until the deodorizing agent 4 reaches a precalibrated minimum.

Figure 2:
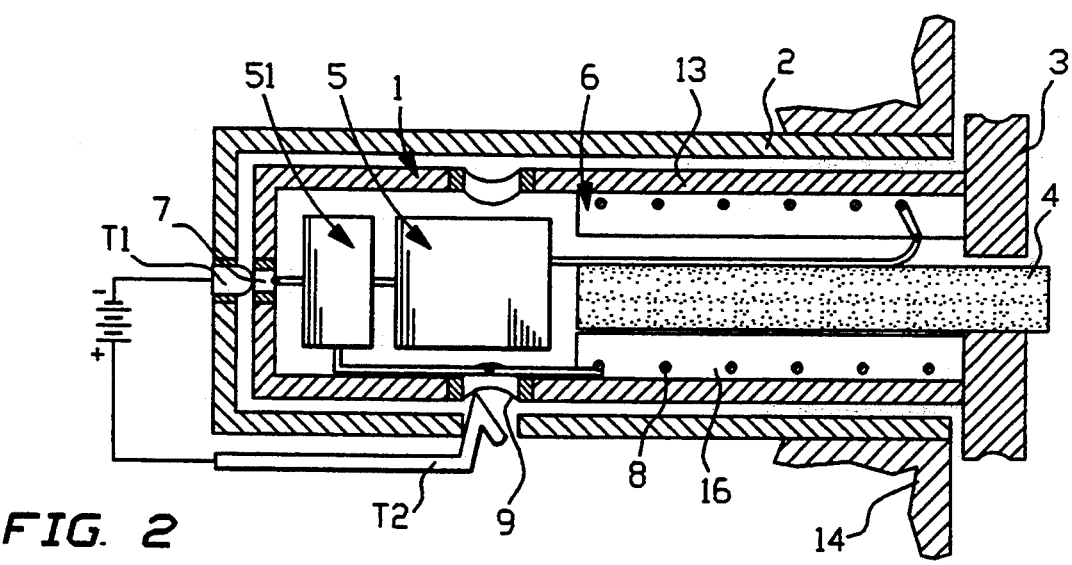
FIG. 2 shows the device with automatic electrical power controller and timer.

Another preferred embodiment of the device 1 is depicted in FIG. 2. This embodiment comprises a timer 51 which automatically opens and closes power to the power controller 5 at predetermined intervals. The intervals can be set by a means for adjustment. In this way, the energizing of heating unit 6—and thereby the vaporization of deodorizing agent 4—can be moderated. Thus, as with the embodiments of FIG. 1, 1A, 1B and 1C, the device can remain in socket 2 in constant contact with terminals T1 and T2, and release a pleasant fragrance without affirmative action from the user.

Figure 3:
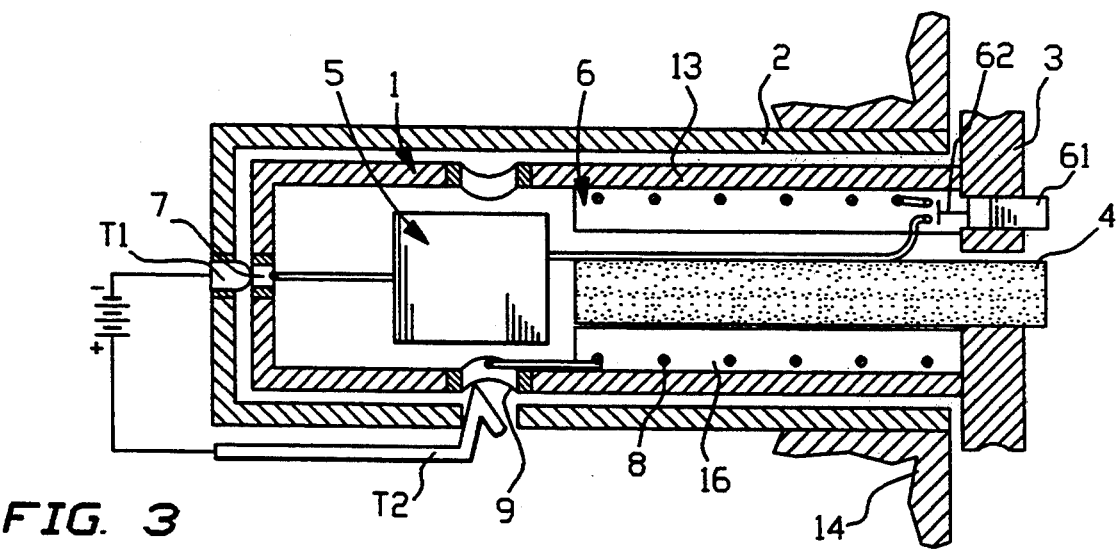
FIG. 3 shows the device with automatic electrical power controller and manual override switch.
Figure 4:
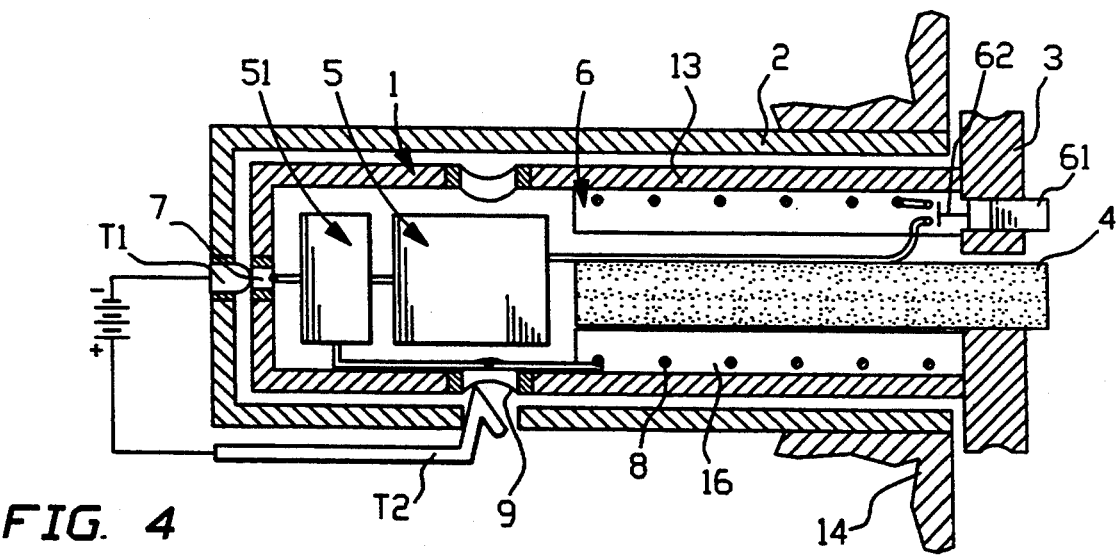
FIG. 4 shows the device with automatic electrical power controller, manual override switch and timer.

FIG. 3 shows another preferred embodiment of the device 1 which uses an override switch 62 activated through button to open the electric circuit. This embodiment allows the operator to disable the device, but nevertheless leave it in place within socket 2. FIG. 4 shows an embodiment which utilizes the timer 51 explained above as shown in FIG. 2 in combination with the override switch 62 and button 61 explained above as shown in FIG. 3.

FIGS. 1, 1A, 1B, 1C, 2, 3 and 4 present various embodiments of the same invention. These embodiments can be used independent of one another or they can be used in combination. It must be understood that many variations of the invention can be created. The embodiments shown depict the best mode of the invention, but it is obvious that numerous shapes, sizes and orientations can be used for all the parts described. It should be therefore understood that in light of the appended claims, the invention may be practiced other than as specifically described, and individual features described in differing embodiments may be modified, combined or used in orientations other than those shown.

What is claimed is:

1. An automatic motor vehicle deodorizer device, adapted for insertion into a motor vehicle cigarette lighter socket having two terminals to provide electrical energy, which comprises;

(a) a generally cylindrical-fitting housing at least partially insertable into a motor vehicle cigarette lighter socket, and adapted to receive a vaporizable deodorizing agent;

(b) an electrical power controller contained within said housing to automatically open and close an electrical circuit within said housing, the electrical power controller comprises a sensing switch responsive to the quantity of the vaporizable deodorizing agent in the housing, which automatically closes only so long as the vaporizable deodorizing agent in the housing exceeds a precalibrated minimum and which automatically opens when the vaporizable deodorizing agent in the housing falling below the precalibrated minimum;

(c) an electrical heater unit contained within said housing and, when operating, having adequate heating to evaporate a portion of the vaporizable deodorizing agent;

(d) two terminal contacts, each of said two terminal contacts being attached to said housing and being positioned to directly and continuously contact each of two terminals of the motor vehicle cigarette lighter socket when said housing is operably inserted into the motor vehicle cigarette lighter socket having two terminals;

(e) the electrical circuit running from each of said two terminal contacts and running to said electrical power controller and to said electrical heater unit such that said electrical power controller may automatically turn the electrical heater unit off and on by breaking and completing said circuit when said housing is operably inserted into the motor vehicle cigarette lighter socket.

2. The device recited in claim 1 further comprising a timer connected to turn on and off the electrical circuit.

3. The device recited in claim 1 further comprising an override switch connected in series with the electrical circuit.

4. The device recited in claim 3 further comprising a timer connected to turn on and off the electrical circuit.

5. The device recited in claim 1 where the sensing switch further comprises:

(a) a sensing conductor having an attached end and a movable end, the attached end electrically connected to one end of the electrical power controller;

(b) a supply conductor having an attached end and a contact end, the attached end electrically connected to an other end of the electrical power controller;

(c) a means to bias the sensing conductor against the vaporizable deodorizing agent so that the position of the movable end of the sensing conductor varies as the amount of the vaporizable deodorizing agent in the housing varies;

(d) the contact end of the supply conductor and the movable end of the sensing conductor adapted so that the contact end of the supply conductor and the movable end of the sensing conductor are electrically connected only so long as the vaporizable deodorizing agent in the housing exceeds the pre-calibrated minimum.

6. The device recited in claim 5 further comprising a timer connected to turn on and off the electrical circuit.

7. The device recited in claim 5 further comprising an override switch connected in series with the electrical circuit.

8. The device recited in claim 7 further comprising a timer connected to turn on and off the electrical circuit.

9. The device recited in claim 5 where the means to bias the sensing conductor against the vaporizable deodorizing agent comprises a forcing means urging the sensing conductor against the vaporizable deodorizing agent.

10. The device recited in claim 9 further comprising an override switch connected in series with the electrical circuit.

11. The device recited in claim 10 further comprising a timer connected to turn on and off the electrical circuit.

12. The device recited in claim 9 further comprising a timer connected to turn on and off the electrical circuit.

13. The device recited in claim 5 where the means to bias the sensing conductor against the vaporizable deodorizing agent comprises the sensing conductor.

14. The device recited in claim 13 further comprising a timer connected to turn on and off the electrical circuit.

15. The device recited in claim 13 further comprising an override switch connected in series with the electrical circuit.

16. The device recited in claim 15 further comprising a timer connected to turn on and off the electrical circuit.

* * * * *